(12) United States Patent
Dong

(10) Patent No.: US 11,874,412 B2
(45) Date of Patent: *Jan. 16, 2024

(54) SYSTEM AND METHOD FOR PET DATA CORRECTION

(71) Applicant: SHANGHAI UNITED IMAGING HEALTHCARE CO., LTD., Shanghai (CN)

(72) Inventor: Xiaoxia Dong, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 221 days.

This patent is subject to a terminal disclaimer.

(21) Appl. No.: 17/446,461

(22) Filed: Aug. 30, 2021

(65) Prior Publication Data
US 2021/0389484 A1    Dec. 16, 2021

Related U.S. Application Data

(63) Continuation of application No. 16/586,701, filed on Sep. 27, 2019, now Pat. No. 11,105,939, which is a (Continued)

(30) Foreign Application Priority Data

Aug. 15, 2016 (CN) .......................... 201610668696.4

(51) Int. Cl.
G01T 1/29 (2006.01)
G06T 11/00 (2006.01)
(Continued)

(52) U.S. Cl.
CPC ............ *G01T 1/2985* (2013.01); *A61B 6/037* (2013.01); *G06F 17/18* (2013.01); *G06T 11/005* (2013.01); *G06T 11/006* (2013.01)

(58) Field of Classification Search
None
See application file for complete search history.

(56) References Cited

U.S. PATENT DOCUMENTS 7,917,192 B2   3/2011   Dos Santos Varela
8,193,505 B2   6/2012   Watson et al.
(Continued)

FOREIGN PATENT DOCUMENTS

CN   101156780 A   4/2008
CN   102324089 A   1/2012
(Continued)

OTHER PUBLICATIONS

International Search Report in PCT/CN2017/096642 dated Nov. 13, 2017, 4 pages.
(Continued)

*Primary Examiner* — Hoon K Song
(74) *Attorney, Agent, or Firm* — METIS IP LLC

(57) ABSTRACT

A method for correcting PET data includes acquiring first PET data at a time interval. The method also includes acquiring a first normalization coefficient corresponding to the first PET data. The method also includes determining a scale factor based at least partially on the first normalization coefficient. The method also includes determining second PET data based on the first PET data, the scale factor, and the second normalization coefficient. The method also includes determining a first dead time correction coefficient corresponding to the second PET data. The method also includes determining third PET data based on the second PET data and the first dead time correction coefficient. The method further includes reconstructing a first image based on the third PET data.

19 Claims, 12 Drawing Sheets

Related U.S. Application Data continuation of application No. 15/569,403, filed as application No. PCT/CN2017/096642 on Aug. 9, 2017, now Pat. No. 10,429,525.

(51) Int. Cl.
*A61B 6/03* (2006.01)
*G06F 17/18* (2006.01)

(56) References Cited

U.S. PATENT DOCUMENTS

| 10,429,525 B2* | 10/2019 | Dong ............... G06F 17/18 |
| 2005/0123090 A1 | 6/2005 | Heismann et al. |
| 2014/0200848 A1 | 7/2014 | Panin et al. |
| 2015/0063529 A1 | 3/2015 | Taguchi et al. |
| 2016/0078646 A1 | 3/2016 | Liu et al. |
| 2019/0049605 A1 | 2/2019 | Dong |

FOREIGN PATENT DOCUMENTS

| CN | 102813527 A | 12/2012 |
| CN | 104183012 A | 12/2014 |
| CN | 105389811 A | 3/2016 |

OTHER PUBLICATIONS

Written Opinion in PCT/CN2017/096642 dated Nov. 13, 2017, 5 pages.
First Office Action in Chinese Application No. 201610668696.4 dated Jun. 4, 2018, 20 pages.
Tetsuya Tsujikawa et al., Does Partial Volume Corrected Maximum SUV Based on Count Recovery Coefficient in 3D-PET/CT Correlate with Clinical Aggressiveness of Non-Hodgkin's Lymphoma?, Annals of Nuclear Medicine, 22(1): 23-30, 2008.
Liu, Li et al., Data Corrections in Positron Emission Tomography (PET), Chinese Journal of Stereology and Image Analysis, 12(2): 147-151, 2007.

* cited by examiner

SYSTEM AND METHOD FOR PET DATA CORRECTION

CROSS-REFERENCE TO RELATED APPLICATIONS

This application is a continuation of U.S. application Ser. No. 16/586,701, filed on Sep. 27, 2019, which is a continuation of U.S. application Ser. No. 15/569,403 (Issued as U.S. Pat. No. 10,429,525), filed on Oct. 26, 2017, which is a U.S. national stage under 35 U.S.C. § 371 of international application No. PCT/CN2017/096642, filed on Aug. 9, 2017, which claims priority of Chinese Patent Application No. 201610668696.4, filed on Aug. 15, 2016, the contents of which are hereby incorporated by reference.

TECHNICAL FIELD

The present disclosure generally relates to data correction, and more particularly to a system and method for normalization correction, as a part of data correction in positron emission tomography.

BACKGROUND

Nuclear medicine tomographic imaging techniques, such as positron emission tomography (PET), use radiation to produce images of a patient. For example, the PET technique may require administration of a radionuclide to the patient. Gamma photons may be emitted by the radionuclide may be used to produce images. During the process of a PET image reconstruction, a normalization correction (e.g., a self-normalization or a component-based normalization) may be needed to deal with non-uniformity of line of response (LOR) in PET data. However, the standardized uptake value (SUV) of a PET image with self-normalization data correction may differ from that of a PET image with a component-based normalization data correction. Thus, there is a need for a system and a method to obtain PET images with same SUVs either by performing a self-normalization or performing a component-based normalization on same PET data.

SUMMARY

In an aspect of the present disclosure, a method may be implemented on at least one computing device, each of which may have at least one processor and storage for correcting PET data. The method may comprise: acquiring first PET data at a time interval; acquiring a first normalization coefficient corresponding to the first PET data; determining a scale factor based at least partially on the first normalization coefficient; determining second PET data based on the first PET data, the scale factor, and the second normalization coefficient; determining a first dead time correction coefficient corresponding to the second PET data; determining third PET data based on the second PET data and the first dead time correction coefficient; and reconstructing a first image based on the third PET data.

In some embodiments, the determining a scale factor based at least partially on the first normalization coefficient may include: acquiring fourth PET data at a plurality of time intervals; acquiring a plurality of first normalization coefficients corresponding to the fourth PET data acquired at the plurality of time intervals, respectively; acquiring a plurality of second normalization coefficients corresponding to the fourth PET data acquired at the plurality of time intervals, respectively; reconstructing a first set of images based on the fourth PET data and the plurality of first normalization coefficients; reconstructing a second set of images based on the fourth PET data and the plurality of second normalization coefficients; determining a set of scale factors based on the first set of images and the second set of images; and determining the scale factor corresponding to the first PET data based on the set of scale factors.

In some embodiments, the plurality of first normalization coefficients may be determined based on a self-normalization correction method, and the plurality of second normalization coefficients may be determined based on a component-based normalization correction method.

In some embodiments, each of the set of scale factors may correspond to a single count rate.

In some embodiments, the set of scale factors may include a set of ratios between grey values of the first set of images and grey values of the second set of images, respectively.

In some embodiments, the determining a scale factor based on the set of scale factors may include: determining a fitted curve based on the set of scale factors; and determining the scale factor based on the fitted curve.

In some embodiments, the determining a scale factor based at least partially on the first normalization coefficient may include: acquiring a line of response counts corresponding to the first PET data; determining a normalized counts based on the line of response counts and the first normalization coefficient; and determining the scale factor based on the line of response counts and the normalized counts.

In some embodiments, the scale factor may be a ratio between the line of response counts and the normalized counts.

In some embodiments, the method may further comprise: determining fifth PET data based on the first PET data, and the first normalization coefficient; determining a second dead time correction coefficient corresponding to the fifth PET data; determining sixth PET data based on the fifth PET data and the second dead time correction coefficient; and reconstructing a second image based on the sixth PET data.

In some embodiments, the second image may have a same standardized uptake value (SUV) as the first image.

In another aspect of the present disclosure, a method may be implemented on at least one computing device, each of which may have at least one processor and storage for correcting PET data. The method may comprise: acquiring PET data at a time interval; acquiring a plurality of correction coefficients, wherein the plurality of correction coefficients may include a normalization coefficient corresponding to the PET data, and a scale factor corresponding to the PET data; correcting the PET data based on the plurality of correction coefficients; and reconstructing an image based on the corrected PET data.

In some embodiments, the normalization coefficient may be determined based on a component-based normalization correction method.

In some embodiments, the acquiring the plurality of correction coefficients may include: acquiring a single count rate at the time interval; and acquiring the plurality of correction coefficients corresponding to the single count rate.

In some embodiments, the acquiring the plurality of correction coefficients corresponding to the single count rate may include: determining a relationship between the single count rate and the plurality of correction coefficients; and determining the plurality of correction coefficients corresponding to the single count rate based on the relationship between the single count rate and the plurality of correction coefficients.

In some embodiments, the determining the relationship between the single count rate and the plurality of correction coefficients may include: acquiring a first look up table, wherein the first look up table may indicate a relationship between the single count rate and the normalization coefficient corresponding to the PET data.

In some embodiments, the determining the relationship between the single count rate and the plurality of correction coefficients may include: acquiring a second look up table, wherein the second look up table may indicate a relationship between the single count rate and the scale factor.

In some embodiments, the second look up table may be determined according to a scale factor determination method. The method may include: determining line of response counts based on the first PET data; determining normalized counts based on the line of response counts and the normalization coefficient; and determining the scale factor corresponding to the first PET data based on the line of response counts and the normalized counts.

In some embodiments, the second look up table may be determined according to a scale factor determination method. The method may include: acquiring second PET data at a plurality of time intervals; acquiring a plurality of first normalization coefficients corresponding to the plurality of time intervals, respectively; acquiring a plurality of second normalization coefficients corresponding to the plurality of time intervals, respectively; reconstructing a first set of images based on the second PET data and the plurality of first normalization coefficients; reconstructing a second set of images based on the second PET data and the plurality of second normalization coefficients; determining a set of scale factors based on the first set of images and the second set of images; and determining a scale factor corresponding to the first PET data based on the set of scale factors.

In some embodiments, the first normalization may be determined based on a self-normalization correction method, and the second normalization coefficient may be determined based on a component-based normalization correction method.

In a further aspect of the present disclosure, a system may be provided. The system may comprise: at least one non-transitory storage medium including a set of instructions for correcting PET data; and at least one processor configured to communicate with the at least one storage media. When executing the set of instructions, the at least one processor may be configured to cause the system to: acquire first PET data at a time interval; acquire a first normalization coefficient corresponding to the first PET data; determine a scale factor based at least partially on the first normalization coefficient; determine second PET data based on the first PET data, the scale factor, and the second normalization coefficient; determine a first dead time correction coefficient corresponding to the second PET data; determine third PET data based on the second PET data and the first dead time correction coefficient; and reconstruct a first image based on the third PET data.

In a further aspect of the present disclosure, a system may be provided. The system may comprise: at least one non-transitory storage medium including a set of instructions for correcting PET data; and at least one processor configured to communicate with the at least one storage media. When executing the set of instructions, the at least one processor may be configured to cause the system to: acquire PET data at a time interval; acquire a plurality of correction coefficients, wherein the plurality of correction coefficients may include a normalization coefficient corresponding to the PET data, and a scale factor corresponding to the PET data; correct the PET data based on the plurality of correction coefficients; and reconstruct an image based on the corrected PET data.

In a further aspect of the present disclosure, a non-transitory computer readable medium may be provided. The non-transitory computer readable medium may store instructions. The instructions, when executed by a computing device, may cause the computing device to implement a method, comprising: acquiring first PET data at a time interval; acquiring a first normalization coefficient corresponding to the first PET data; determining a scale factor based at least partially on the first normalization coefficient; determining second PET data based on the first PET data, the scale factor, and the second normalization coefficient; determining a first dead time correction coefficient corresponding to the second PET data; determining third PET data based on the second PET data and the first dead time correction coefficient; and reconstructing a first image based on the third PET data.

In a further aspect of the present disclosure, a non-transitory computer readable medium may be provided. The non-transitory computer readable medium may store instructions. The instructions, when executed by a computing device, may cause the computing device to implement a method, comprising: acquiring PET data at a time interval; acquiring a plurality of correction coefficients, wherein the plurality of correction coefficients may include a normalization coefficient corresponding to the PET data, and a scale factor corresponding to the PET data; correcting the PET data based on the plurality of correction coefficients; and reconstructing an image based on the corrected PET data.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
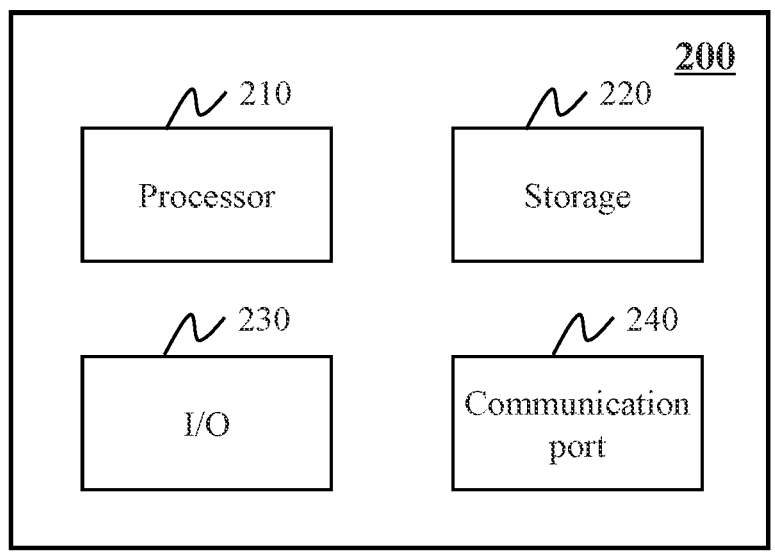
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a positron emission tomography (PET) system, a computed tomography (CT) system, an emission computed tomography (ECT) system, a magnetic resonance imaging (MRI) system, an ultrasonography system, an X-ray photography system, or the like, or any combination thereof.

For illustration purposes, the disclosure is directed to systems and methods for PET data correction. In a PET image reconstruction process, normalization correction (e.g., a self-normalization or a component-based normalization) may be performed to correct PET data. The normalization correction may be used to correct non-uniformity of detectors. To obtain PET images with same SUVs by either performing a self-normalization or performing a component-based normalization on same PET data, a scale factor may be determined in different ways as disclosed in the following embodiments.

Figure 1:
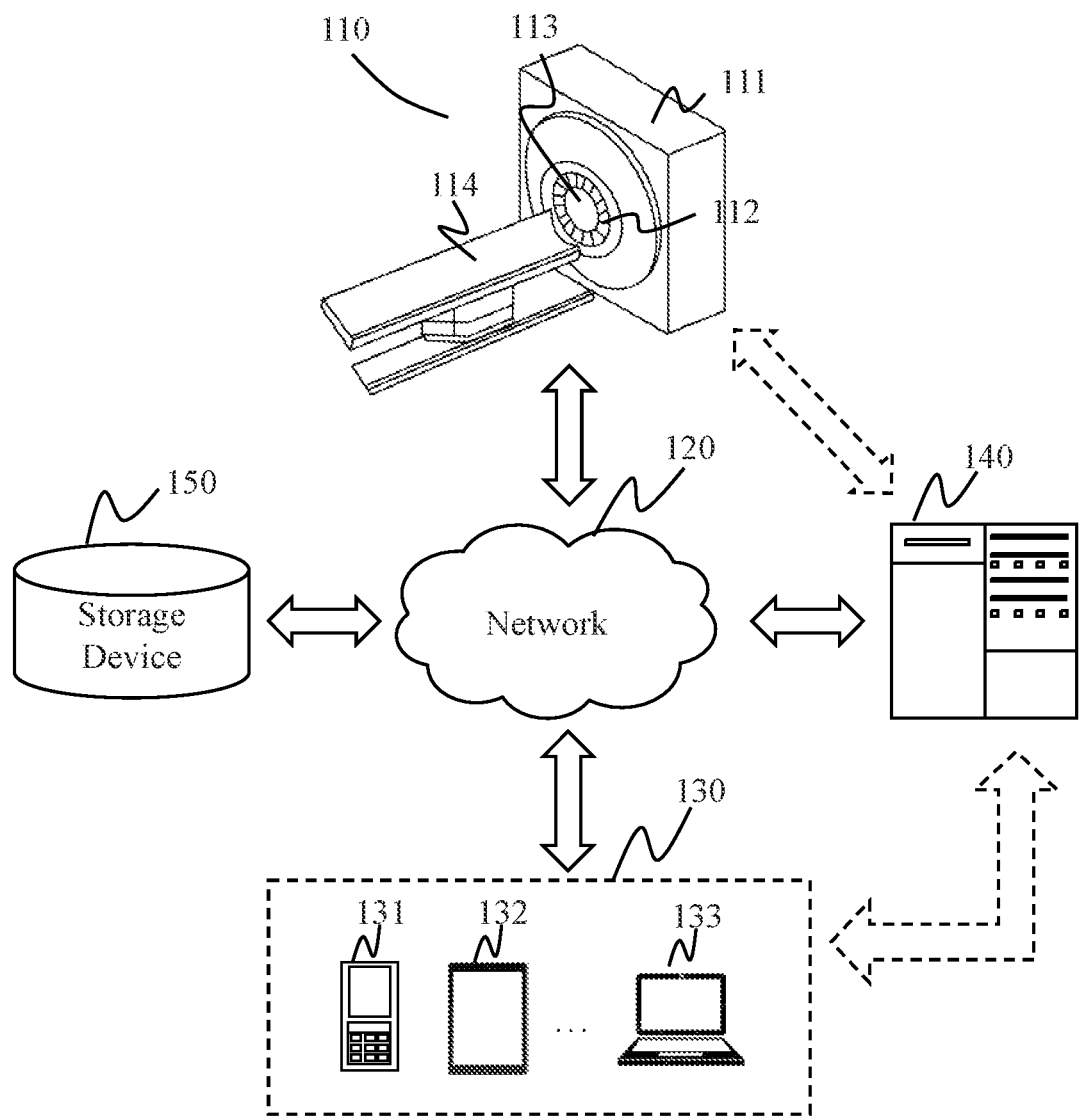
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system 100 may be a single modality system. For example, the imaging system 100 may include a positron emission tomography (PET) system. In some embodiments, the imaging system 100 may be a multi-modality system. For example, the imaging system 100 may include a computed tomography-positron emission tomography (CT-PET) system, a magnetic resonance-positron emission tomography (MR-PET) system, or the like.

As shown in FIG. 1, the Imaging system 100 may include a PET scanner 110, a network 120, one or more terminals 130, a processing engine 140, and a storage device 150. The PET scanner 110 may include a gantry 111, a detector 112, a detecting region 113, and a table 114. A subject may be placed on the table 114 for scanning. Before a PET scan is started, a PET tracer (also referred to as "PET tracer molecules") may be introduced into the subject. The PET tracer may emit positrons as it decays. An annihilation (also referred to as an "annihilation event" or a "coincidence event") may occur when the positron collide to an electron. The annihilation may result in two gamma photons, which may travel in opposite directions. The line connecting the two gamma photons may be referred to as a "line of response (LOR)". The detector 112 may detect the annihilation events (e.g., gamma photons) emitted from the detecting region 113. The gantry 111 may support the detector 112. In some embodiments, the detector 112 may include one or more detector units. The detector units may be implemented in any suitable manner, for example, a ring, a rectangle, or an array. In some embodiments, the detector units may include one or more crystal elements and/or one or more photomultiplier tubes (PMT) (not shown). In some embodiments, a PMT as employed in the present disclosure may be a single-channel PMT or a multi-channel PMT.

The network 120 may include any suitable network that can facilitate exchange of information and/or data for the Imaging system 100. In some embodiments, one or more components of the Imaging system 100 (e.g., the PET scanner 110, the terminal 130, the processing engine 140, the storage device 150, etc.) may communicate information and/or data with one or more other components of the Imaging system 100 via the network 120. For example, the processing engine 140 may obtain image data from the PET scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the Imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information acquired from the PET scanner 110, the terminal 130, and/or the storage device 150. For example, the processing engine 140 may process image data and determine a regularization item that may be used to modify the image data. In some embodiments, the processing engine 140 may be a computer, a user console, a single server or a server group, etc. The server group may be centralized or distributed. In some embodiments, the processing engine 140 may be local or remote. For example, the processing engine 140 may access information and/or data stored in the PET scanner 110, the terminal 130, and/or the storage device 150 via the network 120. As another example, the processing engine 140 may be directly connected to the PET scanner 110, the terminal 130 and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage device 150 may store data, instructions, and/or any other information. In some embodiments, the storage device 150 may store data obtained from the PET scanner 110, the terminal 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the Imaging system 100 (e.g., the processing engine 140, the terminal 130, etc.). One or more components in the Imaging system 100 may access the data or instructions stored in the storage device 150 via the network 120. In some embodiments, the storage device 150 may be directly connected to or communicate with one or more other components in the imaging system 100 (e.g., the processing engine 140, the terminal 130, etc.). In some embodiments, the storage device 150 may be part of the processing engine 140.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data acquired from the PET scanner 110, the terminal 130, the storage device 150, and/or any other component of the Imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the PET scanner 110, the terminal 130, the storage device 150, and/or any other component of the Imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the PET scanner 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
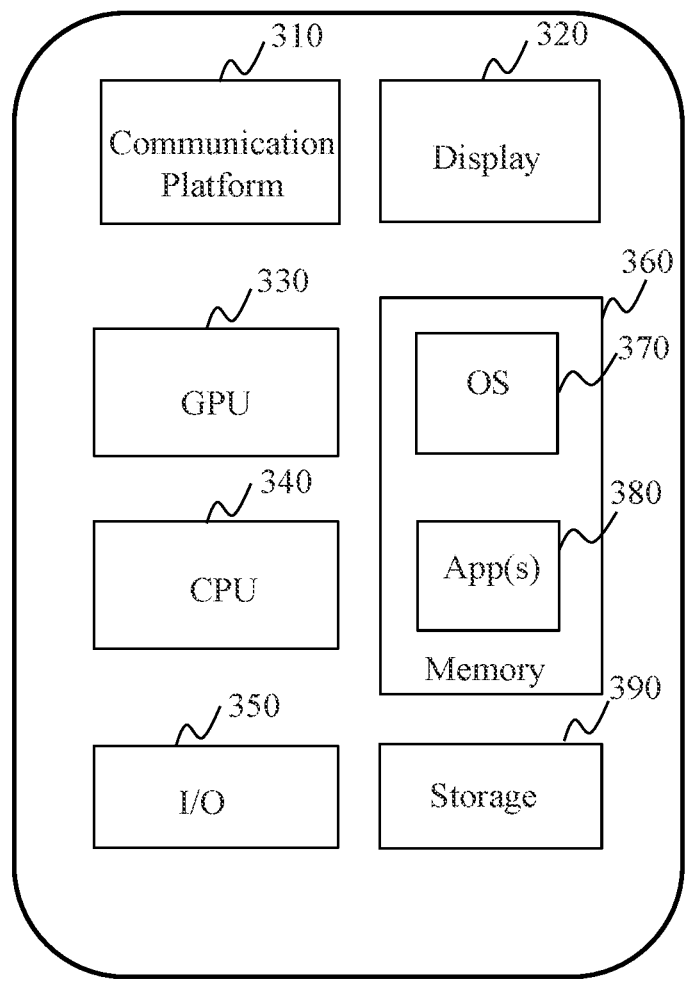
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the Imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
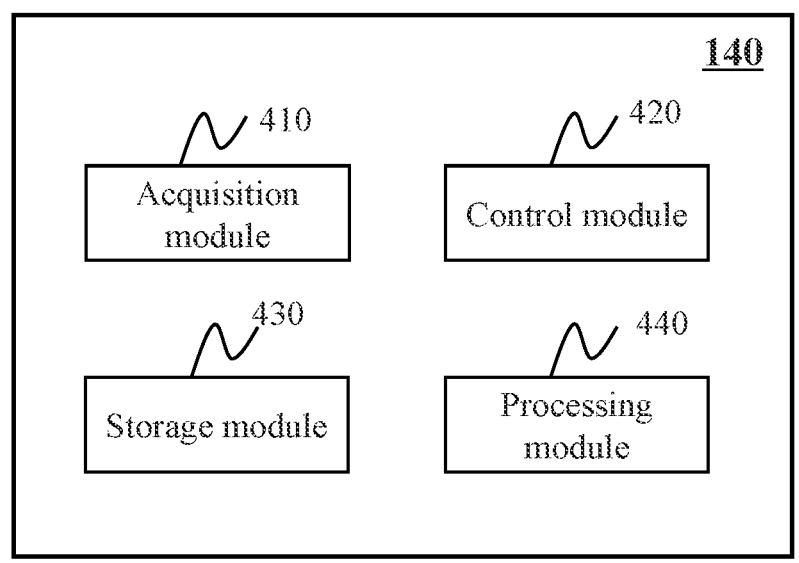
FIG. 4 is a block diagram illustrating an exemplary processing engine according to some embodiments of the present disclosure.

FIG. 4 is a block diagram illustrating an exemplary processing engine 140 according to some embodiments of the present disclosure. The processing engine 140 may include an acquisition module 410, a control module 420, a storage module 430, and a processing module 440.

The acquisition module 410 may acquire data. The acquisition module 410 may acquire data from the PET scanner 110, the network 120, the terminal 130, the storage device 150, or any devices or components disclosed in the present disclosure capable of storing data. The acquired data may include original PET data, processing results (e.g., a PET image), user instructions, algorithms, or the like, or a combination thereof. In some embodiments, the acquisition module 410 may acquire PET data from the PET scanner 110, more particularly, from the PET detector 112. The PET data may include trajectory and/or information of gamma photons generated in an annihilation event at a time interval or at multiple time intervals. As used herein, the time interval may refer to a period of time (e.g., 1 second, 5 seconds, 2 minutes, etc.) during a PET scan. In some embodiments, the PET data may include a list of annihilation events, transverse and longitudinal positions of the LORs at a time interval or at multiple time intervals, or the like, or a combination thereof. In some embodiments, the PET data may be or include single counts and/or LOR counts. The single counts may refer to the count of single events at a time interval. The LOR counts may refer to count of coincidence events at a time interval. The acquisition module 410 may transmit the acquired PET data to a storage device (e.g., the storage module 430 and the storage device 150 etc.) for storage. The PET data may be stored in forms of voxel information, count information, image, vector, or the like, or any combination thereof. In some embodiments, the acquisition module 410 may transmit the acquired PET data to a computing device (e.g., the processing module 440) for processing.

The control module 420 may control operations of one or more modules. Merely for illustration purposes, the control module 420 may control operations of the acquisition module 410, the storage module 430, and/or the processing module 440 (e.g., by generating one or more control parameters). For example, the control module 420 may control the acquisition module 410 to acquire PET data and determine the timing of the acquisition of the PET data. As another example, the control module 420 may control the processing module 440 to process the PET data acquired by the acquisition module 410. In some embodiments, the control module 420 may receive a real-time command or retrieve a predetermined command provided by a user (e.g., a doctor) to control one or more operations of the acquisition module 410 and/or the processing module 440. For example, the control module 420 can adjust the acquisition module 410 and/or the processing module 440 to generate images of a subject according to the real-time command and/or the predetermined command. In some embodiments, the control module 420 may communicate with one or more other devices or modules of the imaging system 100 for exchanging information and/or data.

The storage module 430 may store data. Merely by ways of example, the storage module 430 may store PET data, control parameters, processed PET data, data correction algorithms, PET images, or the like, or a combination thereof. In some embodiments, the storage 430 may store one or more programs and/or instructions that may be executed by the processor(s) of the processing engine 140 to perform exemplary methods described in this disclosure. For example, the storage 430 may store program(s) and/or instruction(s) that can be executed by the processor(s) of the processing engine 140 to determine a PET data correction coefficient, reconstruct a PET image based on the PET data correction coefficient, and/or display any intermediate result or a resultant image.

The processing module 440 may process data provided by various modules of the processing engine 140. The processing module 440 may process PET data acquired by the acquisition module 410, or retrieved from the storage module 430, etc. The processing module 440 may process the obtained data by performing a plurality of operations. Exemplary data processing operations may include low pass filtering, normalization, dead-time correction, image reconstruction, etc. In some embodiments, the processing module 440 may determine a data correction algorithm, and correct PET data based on the data correction coefficient. In some embodiments, the processing module 440 may determine a normalization coefficient to correct the PET data. The normalization coefficient may be determined according to normalization corrections of various types. Exemplary normalization may include self-normalization, component-based normalization, etc. For example, a self-normalization coefficient (also referred to as "self-norm coefficient") may be determined based on a self-normalization. As another example, a component-based normalization coefficient (also referred to as "component-norm coefficient") may be determined based on a component-based normalization. In some embodiments, the processing module 440 may determine a comprehensive correction coefficient (e.g., a scale factor) to correct the PET data. The scale factor may be obtained based on one or more correction coefficients, such as a self-norm coefficient, or a component-norm coefficient, etc. The corrected PET data may be stored in a storage device (e.g., the storage module 430 and the storage device 150 etc.). In some embodiments, the corrected PET data may be reconstructed to obtain a PET image.

In some embodiments, the processing module 440 may reconstruct PET images, based on the PET data, according to a reconstruction algorithm, generate reports including one or more PET images and/or other related information, and/or perform any other function for image reconstruction in accordance with various embodiments of the present disclosure. Exemplary image reconstruction algorithms may include an analytic reconstruction algorithm, an iterative reconstruction algorithm, etc. Exemplary analytic reconstruction algorithms may include a filter back projection (FBP) algorithm, a back projection filter (BFP) algorithm, a p-filtered layer gram, or the like, or any combination thereof. Exemplary iterative reconstruction algorithms may include a Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or any combination thereof.

In some embodiments, one or more modules illustrated in FIG. 4 may be implemented in at least part of the exemplary imaging system as illustrated in FIG. 1 or 2. For example, the acquisition module 410, the control module 420, the storage module 430, and/or the processing module 440 may be integrated into a console (not shown). Via the console, a user may set parameters for scanning an object, controlling imaging processes, correcting PET data, controlling parameters for reconstruction of an image, viewing reconstructed images, etc.

Figure 5:
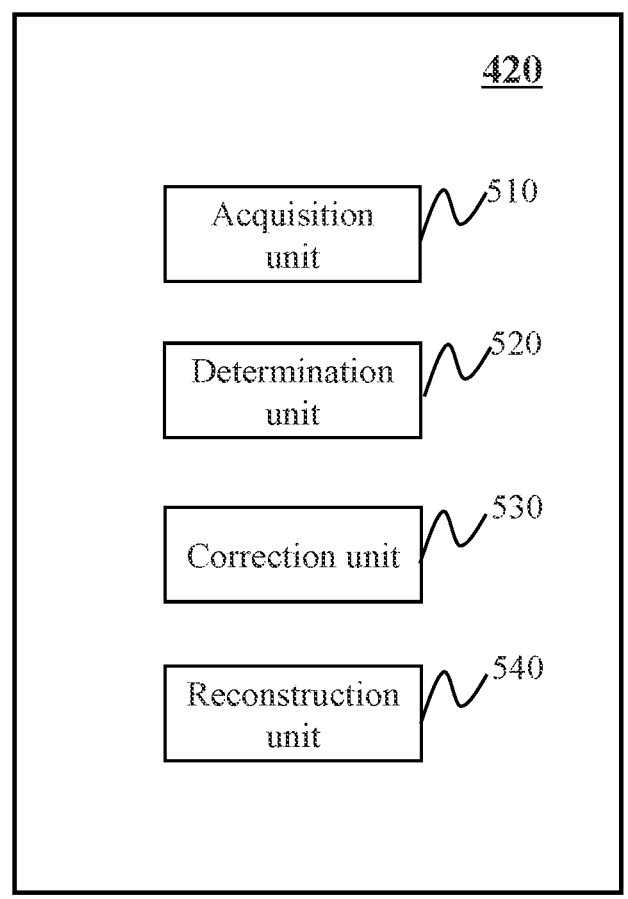
FIG. 5 is a block diagram illustrating an exemplary processing module according to some embodiments of the present disclosure.

FIG. 5 is a block diagram illustrating an exemplary processing module 420 according to some embodiments of the present disclosure. The processing module 420 may include an acquisition unit 510, a determination unit 520, a correction unit 530 and a reconstruction unit 540. The one or more units in the processing module 420 may be implemented on various components (e.g., the processor 210 of the computing device 200 as illustrated in FIG. 2) in the present disclosure.

The acquisition unit 510 may acquire PET data. In some embodiments, the PET data may be original projection data acquired from the PET detector 112. In some embodiments, the PET data may be acquired from a storage device (e.g., the storage module 430, the storage device 150 etc.). For example, the PET data may be original PET data acquired from the PET detector 112. As another example, the acquired PET data may be processed by the processing engine 140. The PET data may include trajectory and/or information of gamma photons generated in annihilations at a time interval or at multiple time intervals. As used herein, the time interval or multiple time intervals may refer to time periods (e.g., 1 second, 2 seconds, etc.) in a PET scan. For example, the PET data may include single counts of the annihilation events during 1 minute. In some embodiments, the PET data may be acquired in forms of count information, vectors, matrixes or the like, or any combination thereof. In some embodiments, the acquisition unit 510 may transmit the acquired PET data to the correction unit 530 for correction. In some embodiments, the acquisition unit 510 may transmit the acquired PET data to the reconstruction unit 540 for image reconstruction.

The determination unit 520 may determine one or more correction coefficients. The correction coefficients may be used to correct the PET data acquired from the acquisition unit 510. The correction coefficients may include a normalization coefficient, a dead time correction coefficient, a scale factor, or the like, or any combination thereof. The normalization coefficient may be used to correct the non-uniformity in the signal response of the detector 112. The dead time correction coefficient may be used to correct the response delay of the detector 112 when collecting radiation photons. The scale factor may be used to scale PET data corrected by different normalizations to obtain images with same SUVs. A normalization coefficient may be either a self-norm coefficient, or a component-norm coefficient. The self-norm coefficient may refer to a normalization coefficient determined based on a self-normalization. The component-norm coefficient may refer to a normalization coefficient determined based on a component-based normalization.

In some embodiments, the determination unit 520 may determine a correction coefficient by receiving a user input or retrieving a correction coefficient from a storage device. For example, the determination unit 520 may obtain one or more correction coefficients from storage devices, such as the storage device 150, the storage module 430, or the like, or any combination thereof. In some embodiments, the determination unit 520 may determine a correction coefficient based on a plurality of algorithms, function, and/or particular operations. For example, the determination unit 520 may determine a correction coefficient with one or more methods described in connection with FIGS. 7A and 7B.

The correction unit 530 may correct the PET data. The correction unit 530 may obtain one or more correction coefficients from the determination unit 520, and correct the PET data acquired from the acquisition unit 510 based on the one or more correction coefficients. For example, a self-norm correction may be performed on the PET data based on a self-norm coefficient acquired from the determination unit 520. As another example, component-based normalization may be performed on the PET data based on a component-norm coefficient acquired from the determination unit 520. In some embodiments, the correction unit 530 may transmit the corrected PET data into a storage device (e.g., the storage module 430, the storage device 150 etc.) for data storage. In some embodiments, the correction unit 530 may transmit the corrected PET data to the reconstruction unit 540 for image reconstruction.

The reconstruction unit 540 may reconstruct an image. The reconstruction unit 540 may obtain corrected PET data from the correction unit 530, and reconstruct a PET image based on the corrected PET data. In some embodiments, the reconstruction unit 540 may reconstruct a set of PET images based on multiple set of PET data generated at multiple time intervals.

It should be noted that the above description of the processing module 440 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, at least one of the plurality of units in the processing module 440 may include a storage unit (not shown). As another example, any one of the plurality of units in the processing module 440 may be divided into two or more sub-units or blocks.

Figure 6:
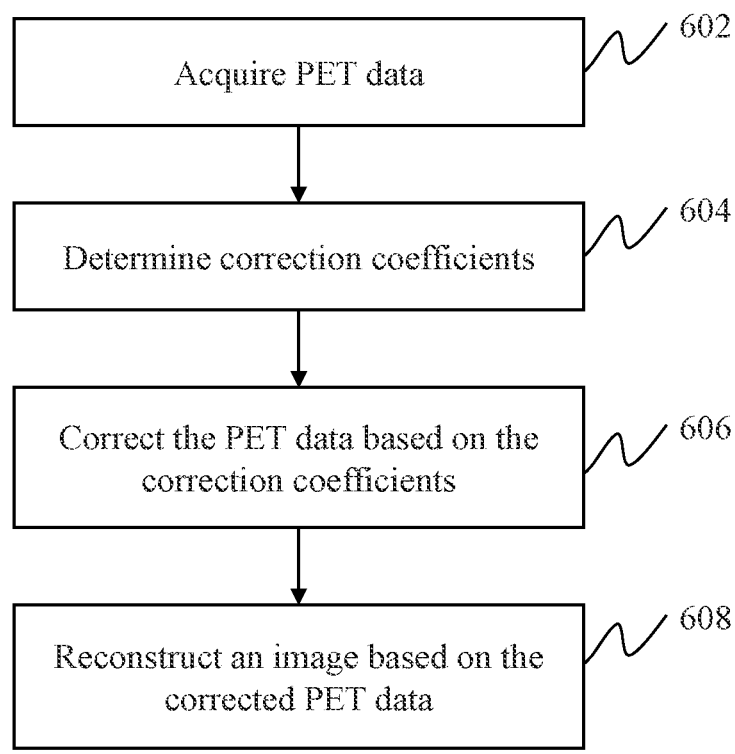
FIG. 6 is a flowchart illustrating an exemplary process for correcting PET data according to some embodiments of the present disclosure.

FIG. 6 is a flowchart illustrating an exemplary process for correcting PET data according to some embodiments of the present disclosure. In some embodiments, the process 600 may be executed by the processing module 420. For example, the process 600 may be implemented as a set of instructions stored in storage device 150, and/or storage 220. The processing engine 140 and/or the CPU 340 may execute the set of instructions and may accordingly be directed to perform the process 600.

In 602, PET data may be acquired. The PET data may be acquired by, for example, the acquisition unit 510. The PET data may be obtained in a PET scan performed on a subject (e.g., a patient). The PET data may include a list of annihilation events, transverse and longitudinal positions of the LORs, or the like, or a combination thereof. In some embodiments, the PET data may be single count rate of annihilation events. In some embodiments, the PET data may be acquired at a certain time interval or at multiple time intervals. For example, the acquisition unit 510 may acquire a set of original PET data from the detector 112 at multiple time intervals. The PET data acquired at multiple time intervals may indicate the variation of the distribution of the PET tracer molecules and/or the coincidence over a period. In some embodiments, the acquired PET data may be pre-processed, for example, by the processing module 440, to remove errors in the PET data.

In 604, correction coefficients may be determined. The correction coefficients may be determined by, for example, the determination unit 520. The correction coefficients may include a normalization coefficient, a dead time correction coefficient, a scale factor, or the like, or any combination thereof. As used herein, a normalization coefficient may refer to a self-norm coefficient or a component-norm coefficient. The scale factor may be used to scale the PET data corrected using different normalization coefficients (e.g., a self-norm coefficient or a component-norm coefficient) to obtain PET images with same SUVs. The dead time correction coefficients may be used to correct the response delay of the detector in a PET scan.

Merely for illustration purposes, a normalization correction coefficient may be determined by performing a plurality of tests on the detector 112. The detector 112 may acquire PET data from a known radioactive source with uniform radiation intensity over a time period. The determination unit 520 may determine an average value of coincidence counts in a detecting region, and coincidence counts of every pair of detectors over the time period. The determination unit 520 may determine the normalization coefficient of a pair of detectors as a ratio between the coincidence counts of the pair of detectors and the average value of coincidence counts in the detecting region. In some embodiments, the plurality of tests may be performed by the processing module 440.

The dead time correction coefficients may be provided in a look-up table (also referred as "LUT"). The LUT may indicate a correspondence relationship between PET data (e.g., single count rate) and dead time correction coefficients. For example, given PET data corrected by a self-norm coefficient, the corresponding dead time correction coefficient may be determined by checking the LUT. As another example, given PET data corrected by component-norm coefficient, the corresponding dead time correction coefficient may be determined by checking the LUT.

In some embodiments, a scale factor corresponding to PET data acquired at a time interval may be determined. In some embodiments, a set of scale factors may be determined. Each of the set of scale factors may correspond to PET data acquired at a time interval. Detail regarding the determination of the scale factor may be disclosed elsewhere in the present disclosure, for example, FIGS. 8 and 9, and the descriptions thereof.

In 606, PET data may be corrected based on the determined correction coefficients. The PET data may be corrected by, for example, the correction unit 530, based on the determined correction coefficients. The correction coefficients may include normalization coefficients, dead time correction coefficients, scale factors, or the like, or any combination thereof. In some embodiments, the PET data may be corrected based on the correction coefficients, and corrected PET data may be generated.

In 608, an image may be reconstructed based on corrected PET data. The image may be reconstructed by, for example, the reconstruction unit 540. In some embodiments, various image reconstruction techniques may be used to reconstruct a PET image based on the corrected PET data. Exemplary image reconstruction techniques may include Fourier reconstruction, constrained image reconstruction, analytic reconstruction, iterative reconstruction, or the like, or any combination thereof. Exemplary analytic reconstruction algorithms may include a filter back projection (FBP) algorithm, a back projection filter (BFP) algorithm, a p-filtered layer gram, or the like, or any combination thereof. Exemplary iterative reconstruction algorithms may include a Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or any combination thereof.

In some embodiments, the process 600 may be an iterative process or a cyclic process including a plurality of iterations. During the plurality of iterations, PET data may be acquired at multiple time intervals. The PET data and/or correction coefficients corresponding to the PET data may be adjusted in the plurality of iterations. After the plurality of iterations, the corrected PET data may be generated. And one or more images corresponding to the multiple time intervals may be reconstructed based on corrected PET data. In some embodiments, the images may have a same SUV.

It should be noted that the above description of the process 600 is provided for the purposes of illustration, not intended to limit the scope of the present disclosure. For persons having ordinary skills in the art, multiple variations and modifications may be reduced to practice in the light of the present disclosure. Merely for illustration purposes, 604 and 606 in the process 600 may be repeated for a plurality of times. For example, a normalization coefficient may be determined in 604. And the PET data (e.g., single counts) may be corrected based on the normalization coefficient in 606. Then the process may return to 604, in which a dead time coefficient may be determined based on the normalized PET data. The normalized PET data may be corrected based on the dead time coefficient in 606.

Figure 7A:
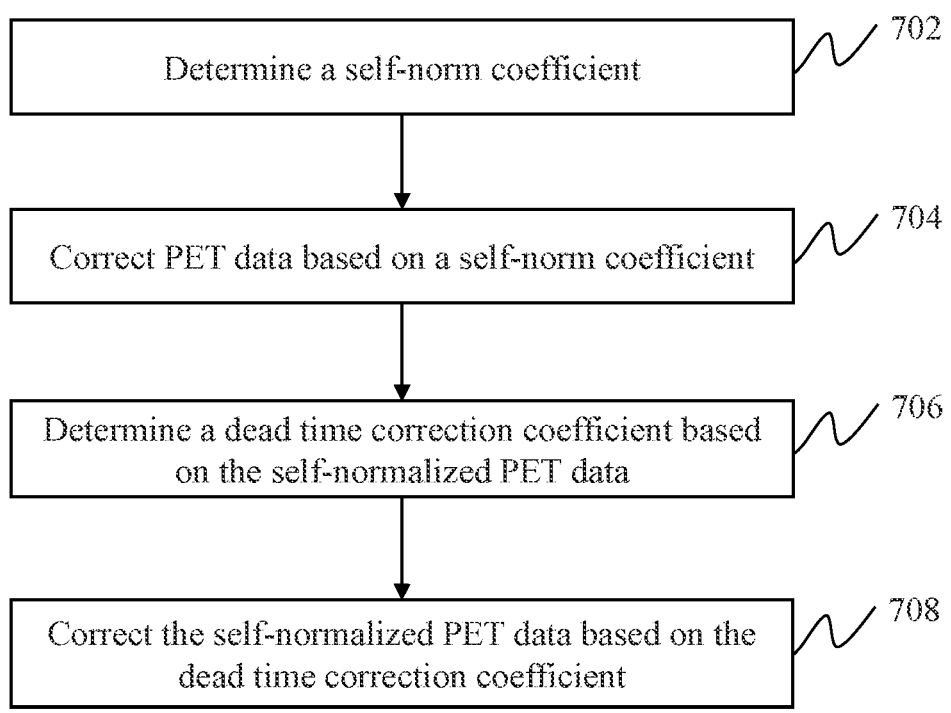
FIG. 7A is a flowchart illustrating an exemplary process for correcting PET data according to some embodiments of the present disclosure.

FIG. 7A is a flowchart illustrating an exemplary process for correcting PET data according to some embodiments of the present disclosure. In some embodiments, the exemplary process 700 may be executed by the processing module 420. For example, the process 700 may be implemented as a set of instructions stored in storage device 150, and/or storage 220. The processing engine 140 and/or the CPU 340 may execute the set of instructions and may accordingly be directed to perform the process 700.

In 702, a self-norm coefficient may be determined. The self-norm coefficient may be determined by, for example, the determination unit 520. In some embodiments, the self-norm coefficient may be determined based on original PET data.

In some embodiments, the self-norm coefficient may be determined according to Equation (1):

$$k_{i,j} = FT^{-1}\{FT[c(i,j)] \cdot h(u,v)\}, \tag{1}$$

where FT is direct Fourier Transform, $FT^{-1}$ is reverse Fourier Transform, $c(i,j)$ is the count of photons from a detector, and $h(u,v)$ denotes the low-pass filter core function.

In 704, PET data may be corrected based on the self-norm coefficient. The PET data may be corrected by, for example, the correction unit 530. The PET data may refer to PET data acquired at a time interval. In some embodiments, the PET data corrected based on the self-norm coefficient (also referred to as "self-normalized PET data") may be obtained by multiplying or dividing the PET data by the self-norm coefficient.

In some embodiments, the PET data corresponding to a time interval may represent single count rate. The single count rate may refer to count of single events at a time interval. The self-normalized PET data (also referred to as "self-normalized single count rate") may be obtained by multiplying or dividing the single count rate by the self-norm coefficient.

In 706, a dead time correction coefficient may be determined based on the self-normalized PET data. The dead time correction coefficient may be determined by, for example, the determination unit 520. In some embodiments, a LUT may be provided to determine the dead time correction coefficient. The LUT may record a correspondence relationship between the dead time correction coefficient and self-normalized single count rate. The dead time correction coefficient may be determined by checking the LUT according to the self-normalized single count rate.

In 708, the self-normalized PET data may be corrected based on the dead time correction coefficient. The self-normalized PET data may be corrected by, for example, the correction unit 530. In some embodiments, the self-normalized PET data which may be further corrected based on the dead time correction coefficient (also referred to as "self-norm corrected PET data") may be obtained by multiplying or dividing the self-normalized PET data by the dead time correction coefficient. The self-norm corrected PET data may be used to reconstruct a self-norm corrected PET image.

It should be noted that the above description of the process 700 is provided for the purposes of illustration, not intended to limit the scope of the present disclosure. For persons having ordinary skills in the art, multiple variations and modifications may be reduced to practice in the light of the present disclosure. For example, a set of PET data acquired at a plurality of time intervals may be corrected according to the method described in the process 700, and a set of self-norm corrected PET data may be determined. The set of self-norm corrected PET data may be used to reconstruct self-norm corrected PET images. However, those variations and modifications do not depart from the scope of the present disclosure.

Figure 7B:
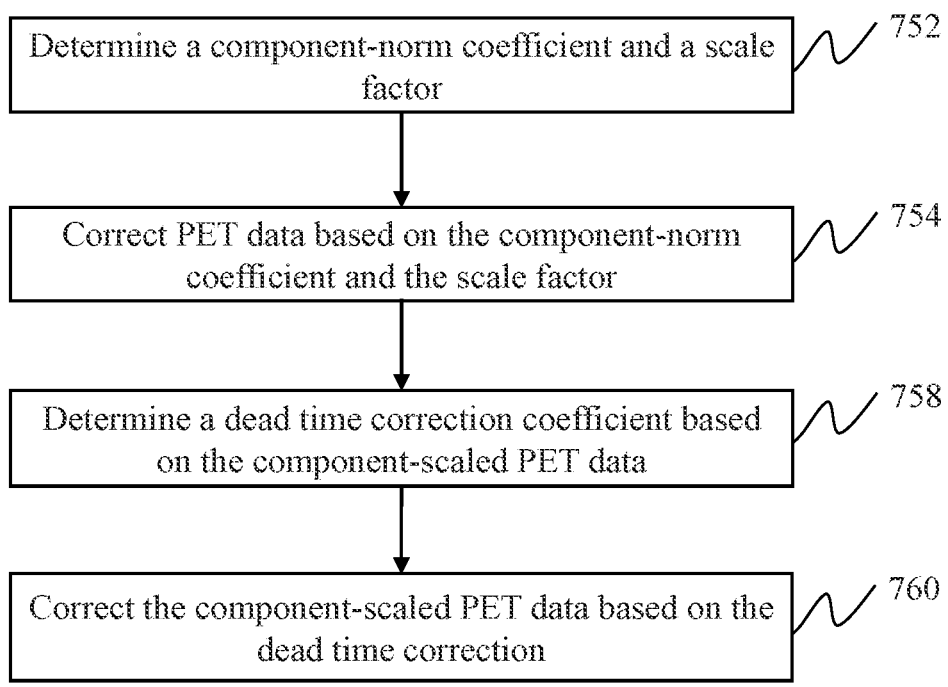
FIG. 7B is a flowchart illustrating an exemplary process for correcting PET data according to some embodiments of the present disclosure.

FIG. 7B is a flowchart illustrating an exemplary process 750 for correcting PET data according to some embodiments of the present disclosure. In some embodiments, the exemplary process 750 may be executed by the processing module 420. For example, the process 750 may be implemented as a set of instructions stored in storage device 150, and/or storage 220. The processing engine 140 and/or the CPU 340 may execute the set of instructions and may accordingly be directed to perform the process 750.

In 752, a component-norm coefficient and a scale factor may be determined.

The component-norm coefficient may be determined by, for example, the determination unit 520. In some embodiments, the component-norm coefficient may be determined based on original PET data.

In some embodiments, the component-norm coefficient may be determined according to Equation (2):

$$NC_{uivj} = \varepsilon_{ui} \cdot \varepsilon_{vj} \cdot c_{uimodD} \cdot c_{vjmodD} \cdot d_{uvrk} \cdot f_{uv} \cdot g_{uvr}, \qquad (2)$$

Where $NC_{uivj}$ is the component-norm coefficient, D is the number of crystals along one side of a block detector, r is the is the radial position of a given line of response (LOR), k is the relative position of the LOR within block detectors, $\varepsilon_{ui}$ and $\varepsilon_{vj}$ represent the intrinsic crystal efficiencies of the crystal i and j in the block detector u and v respectively, $c_{uimodD}$ and $c_{vjmodD}$ represent the systematic variation in efficiency with the relative position of the crystals within each block detector, $d_{uvrk}$ represents the crystal interference factors, $f_{uv}$ represents the axial geometric factors and $g_{uvr}$ represents the radial geometric factors.

The scale factor may be determined based at least partially on the component-norm coefficient. In some embodiments, the scale factor may be determined based on the component-norm coefficient and a self-norm coefficient. The self-norm coefficient and the component-norm coefficient may correspond to same PET data, for example, the PET data acquired at a time interval. Detail regarding the determination of the scale factor may be disclosed elsewhere in the present disclosure, for example, FIGS. 8 and 9, and the descriptions thereof.

In 754, PET data may be corrected based on the component-norm coefficient and the scale factor. The PET data may be corrected by, for example, the correction unit 530. The PET data may refer to PET data acquired at a time interval. In some embodiments, the PET data corrected based on the component-norm coefficient and the scale factor (also referred to as "component-scaled PET data") may be obtained by multiplying or dividing the PET data by the component-norm coefficient and the scale factor.

In some embodiments, the PET data corresponding to a time interval may represent single count rate. The single count rate may be the count rate of single events at the time interval. The component-scaled PET data (also referred to as "component-scaled single count rate") may be calculated by multiplying or dividing the single count rate by the component-norm coefficient and the scale factor.

In 756, a dead time correction coefficient may be determined based on the component-scaled PET data. The dead time correction coefficient may be determined by, for example, the determination unit 520. In some embodiments, a LUT may be provided to determine the dead time correction coefficient. The LUT may record correspondence relationship between dead time correction coefficient and component-scaled single count rate. The dead time correction coefficient may be determined by checking the LUT according to the component-scaled single count rate.

In 758, the component-scaled PET data may be corrected based on the dead time correction coefficient. The component-scaled PET data may be corrected by, for example, the correction unit 530. In some embodiments, the component-scaled PET data which may be further corrected based on the dead time correction coefficient (also referred to "component-scale corrected PET data") may be obtained by multiplied or divided by the component-scaled PET data by the dead time correction coefficient. The component-scale corrected PET data may be used to reconstruct a component-scale corrected PET image.

It should be noted that the above description of the process 750 is provided for the purposes of illustration, not intended to limit the scope of the present disclosure. For persons having ordinary skills in the art, multiple variations and modifications may be reduced to practice in the light of the present disclosure. For example, a set of PET data acquired at a plurality of time intervals may be corrected according to the method described in the process 750, and a set of component-scale corrected PET data may be determined. The set of component-scale corrected PET data may be used to reconstruct component-scale corrected PET images. A component-scale corrected PET image may have a same SUV as a self-norm corrected PET image. However, those variations and modifications do not depart from the scope of the present disclosure. As another example, the component-norm coefficient and the scale factor corresponding to the PET data may also be stored in LUTs. Merely for illustration purposes, a first LUT may be provided for recoding a relationship between single count rate and component-norm coefficients. And a second LUT may be provided for recoding a relationship between single count rate and scale factors.

Figure 8A:
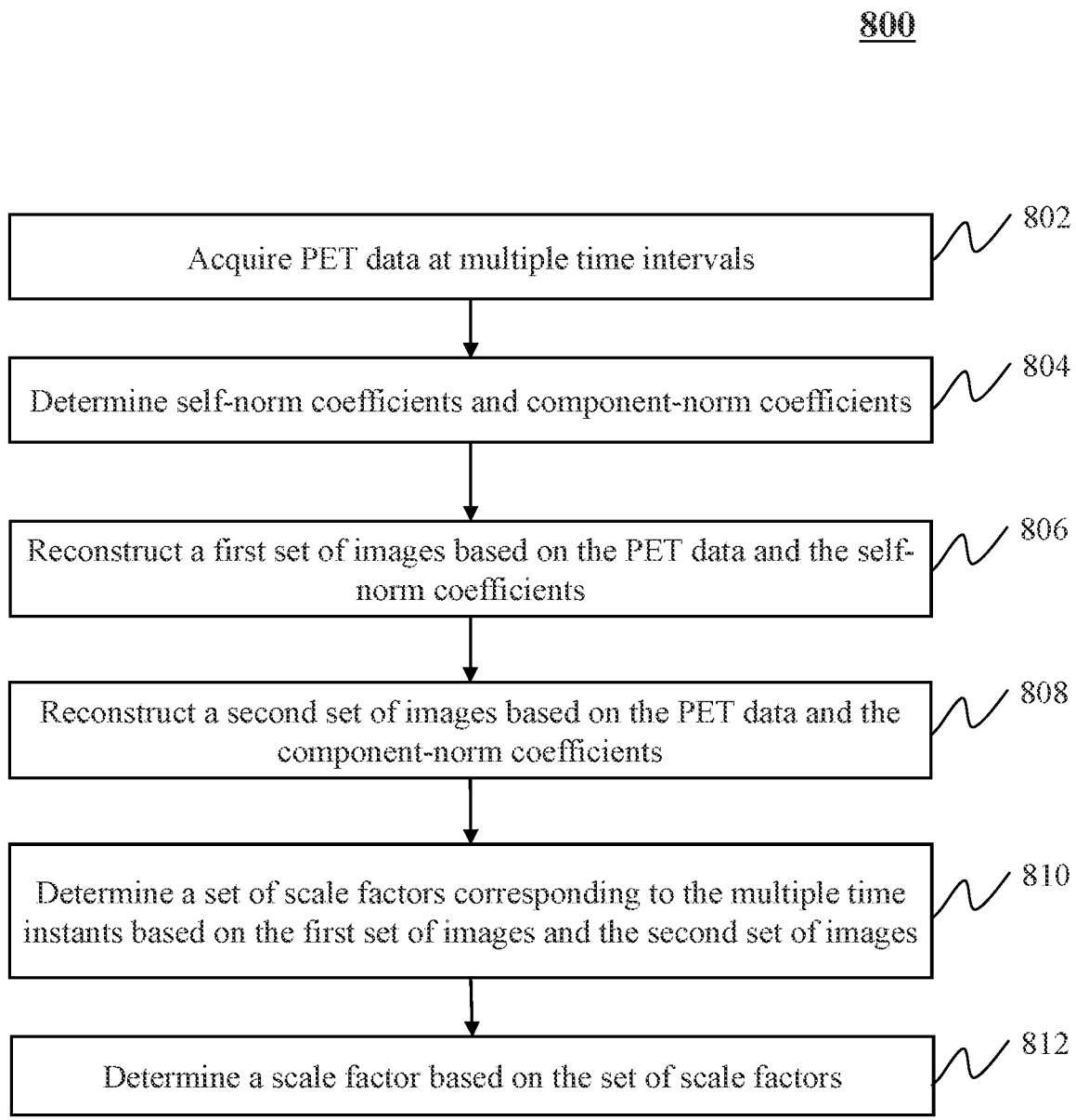
FIG. 8A is a flowchart illustrating an exemplary process for determining a scale factor according to some embodiments of the present disclosure.

FIG. 8 is a flow chart illustrating an exemplary process 800 for determining a scale factor according to some embodiments of the present disclosure. In some embodiments, the process 800 may be executed by the processing module 420. For example, the process 800 may be implemented as a set of instructions stored in storage device 150, and/or storage 220. The processing engine 140 and/or the CPU 340 may execute the set of instructions and may accordingly be directed to perform the process 800.

In 802, PET data may be acquired at multiple time intervals. The PET data may be acquired by, for example the acquisition unit 510. In some embodiments, the PET data may be acquired by scanning a subject (e.g., a water phantom). The subject may have evenly distributed PET tracer molecules therein. The PET data may include PET projection data, such as a list of annihilation events detected by the detector 112. The projection data may further include information on the LOR for each event, such as transverse and longitudinal positions of the LORs, transverse and azimuthal angles, TOF information, or the like, or a combination thereof. In some embodiments, the PET data may be single count rate.

In some embodiments, the PET scanner 110 may obtain PET data at a plurality of time intervals during a PET scan. For example, in a PET scan, the PET scanner 110 may obtain PET data every 10 seconds. The PET data corresponding to the multiple time intervals may be used to determine the distribution of the PET tracer molecules over a time period. The PET data corresponding to the multiple time intervals may be stored in forms of count information, matrix, vector, or the like, or any combination thereof.

In 804, a plurality of self-norm coefficients and component-norm coefficients may be determined. The self-norm coefficients and component-norm coefficients may be determined by, for example, the determination unit 520. In some embodiments, the plurality of self-norm coefficients and component-norm coefficients may correspond to the PET data acquired at the multiple time intervals. More particularly, a self-norm coefficient may correspond to PET data acquired at a certain time interval. Similarly, a component-norm coefficient may correspond to PET data acquired at a certain time interval. The way to determine the self-norm coefficients and the component-norm coefficients may be the same as that to determine a self-norm coefficient and a component-norm coefficient described in 702 of the process 700 and in 752 of the process 750, respectively.

In 806, a first set of images may be reconstructed based on the PET data and the self-norm coefficients. The first set of images may be reconstructed by, for example, the reconstruction unit 540. Each image of the first set of images corresponding to a time interval may be reconstructed based on PET data and a self-norm coefficient. The PET data may be corrected based on the self-norm coefficient before image reconstruction. And PET data corrected based on the self-norm coefficient (i.e., self-normalized PET data) may be determined. The reconstruction unit 540 may reconstruct an image corresponding to the time intervals based on the self-normalized PET data. In some embodiments, the reconstruction unit 540 may reconstruct a first set of images corresponding to the plurality of time intervals based on the self-norm PET data.

In 808, a second set of images may be reconstructed based on PET data and component-norm coefficients. The second set of images may be reconstructed by, for example, the reconstruction unit 540. Each image of the second set of images corresponding to a time interval may be reconstructed based on PET data and a component-norm coefficient. The PET data may be corrected based on the component-norm coefficient before image reconstruction to obtain component-normalized PET data. The reconstruction unit 540 may reconstruct an image corresponding to the time intervals based on the component-normalized PET data. The reconstruction unit 540 may reconstruct a second set of images corresponding to the multiple time intervals based on the component-normalized PET data.

Figure 8B:
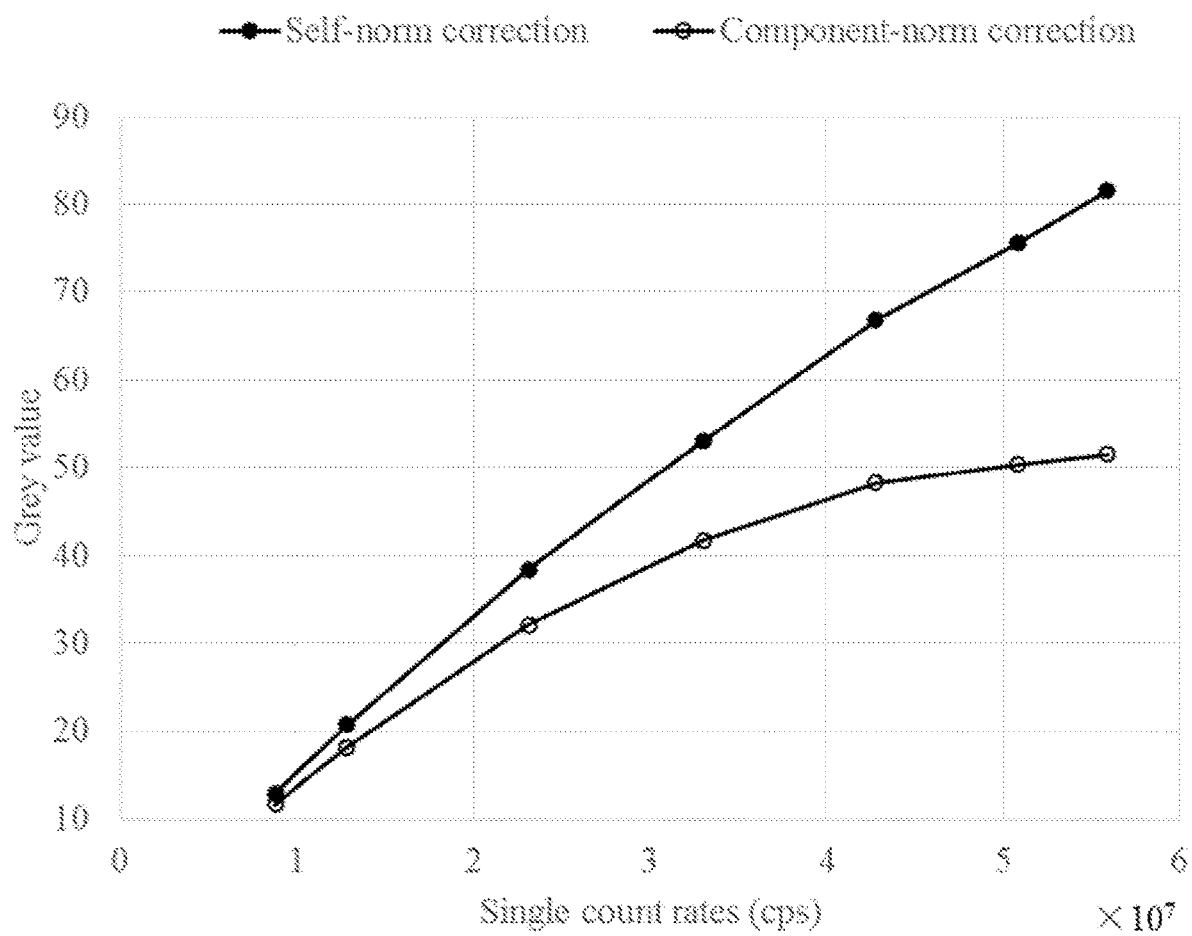
FIG. 8B is a schematic diagram illustrating an exemplary correspondence relationship between the single count rates and the PET image corrected by self-norm and/or component-based normalization according to some embodiments of the present disclosure.

Each pixel or voxel of an image may have a grey value. In some embodiments, an average value of the total grey values of all pixels or voxels of an image in a unit time interval (e.g., 1 second) may be determined as the grey value of the image. As illustrated in FIG. 8B, the first set of images reconstructed based on self-normalized PET data may have grey values shown as the filled circles. The second set of images reconstructed based on component-normalized PET data may have grey values shown as the hollow circles. As shown in the figure, the grey values of the first set of images may differ from that of the second set of images, which may be resulted from different correction coefficients.

In 810, a set of scale factors may be determined based on the first set of images and the second set of images. The set of scale factors may be determined by, for example, the determination unit 520. A scale factor may be determined based on a first image in the first set of images and a second image in the second set of images. Both the first image and the second image may correspond to same PET data. In some embodiments, the scale factor may be a ratio between the grey value of the first image and the grey value of the second image. The set of scale factors may be a set of ratios between grey values of the first set of images and grey values of the second set of images.

Figure 8C:
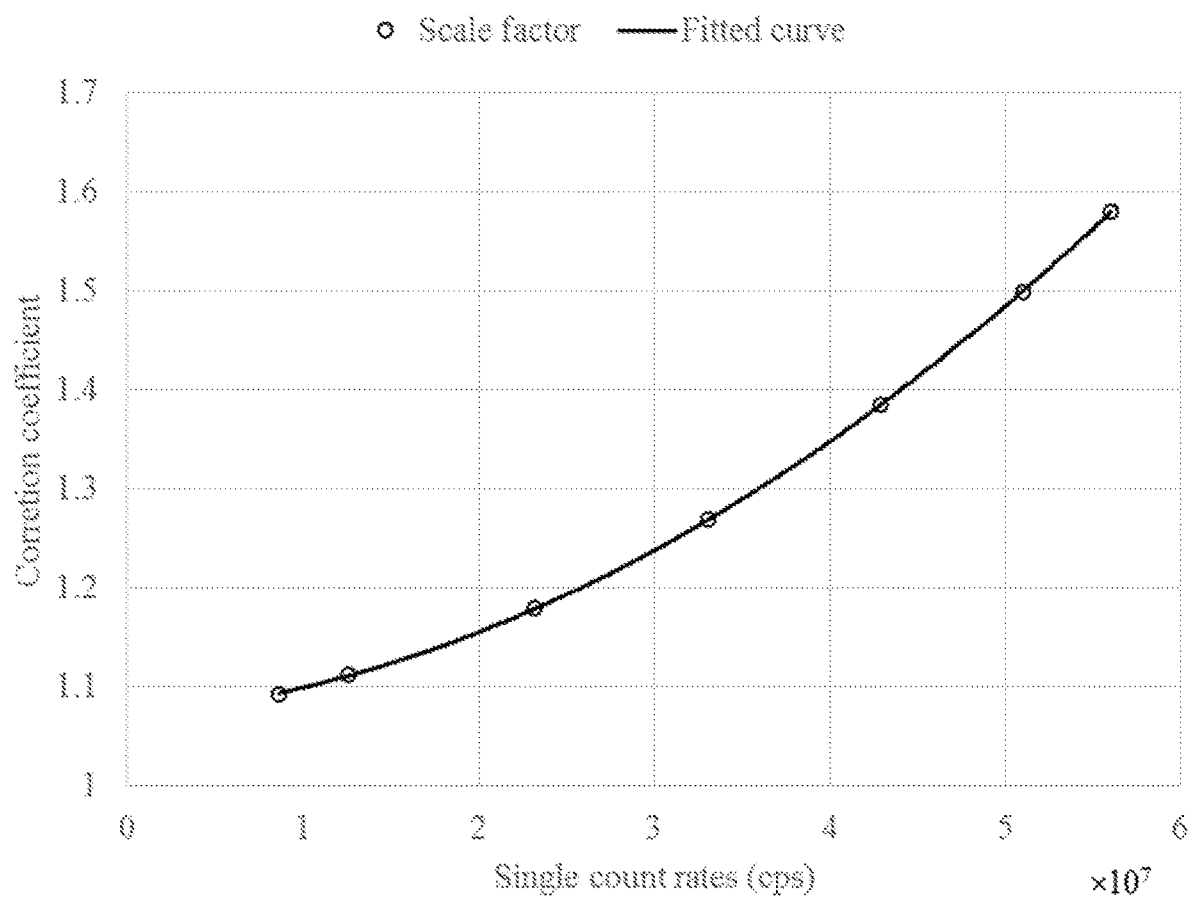
FIG. 8C is a schematic diagram illustrating an exemplary fitted curve between the single count rates and the set of scale factors according to some embodiments of the present disclosure.

The first set of images may correspond to the multiple sets of PET data respectively. Also, the second set of images may correspond to the multiple sets of PET data, respectively. Thus, the set of scale factors may also correspond to the multiple sets of PET data, respectively. The multiple sets of PET data may relate to single count rates, which may vary over time. As shown in FIG. 8C, a fitted curve illustrating the correspondence relationship between the set of scale factors and the single count rates may be generated according to a fitting model (e.g., quadratic fitting). The fitted curve illustrating the correspondence relationship between the set of scale factors and the single count rates may be stored as a LUT in a storage device (e.g., the storage module 440).

In 812, a scale factor may be determined based on the set of scale factors. The scale factor may be determined by, for example, the processing module 420. In some embodiments, a scale factor corresponding to PET data or a single count rate may be determined based on the fitted curve. For example, given component-normalized PET data corresponding to a certain single count or certain a time interval, a scale factor may be determined based on the fitted curve.

In some embodiments, the scale factor may be determined according to one or more algorithms, such as interpolation.

It should be noted that the above description is provided for the purposes of illustration, not intended to limit the scope of the present disclosure. For persons having ordinary skills in the art, multiple variations and modifications may be reduced to practice in the light of the present disclosure. For example, the process 800 may further include an operation for correcting the PET data based on the self-norm coefficients and the component-norm coefficients in 804. The corrected PET data may be reconstructed in 806 and 808 respectively. As another example, the process 800 may further include storing the set of scale factors and/or the fitted curve in a storage device (e.g., the storage module 440). However, those variations and modifications do not depart from the scope of the present disclosure.

Figure 9:
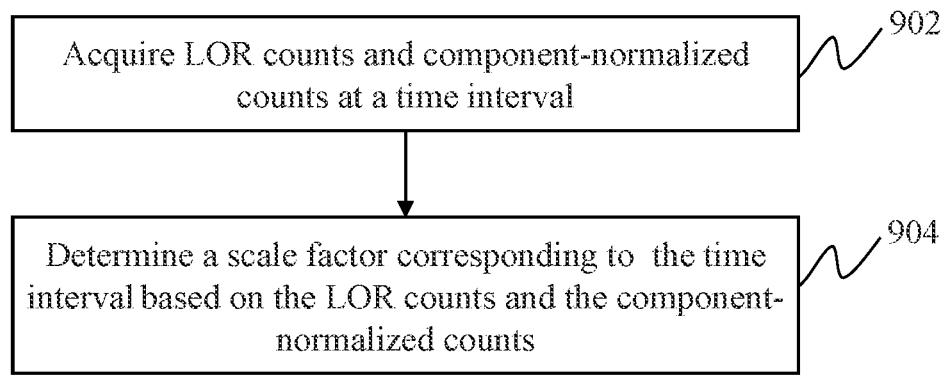
FIG. 9 is a flowchart illustrating an exemplary process for determining a scale factor according to some embodiments of the present disclosure.

FIG. 9 is a flowchart illustrating an exemplary process 900 for determining a scale factor according to some embodiments of the present disclosure. In some embodiments, the process 900 may be executed by the processing module 420. For example, the process 900 may be implemented as a set of instructions stored in storage device 150, and/or storage 220. The processing engine 140 and/or the CPU 340 may execute the set of instructions and may accordingly be directed to perform the process 900.

In 902, LOR counts and component-normalized counts at a time interval may be obtained. The LOR counts may be acquired by, for example, the detector 112 at a time interval. As used herein, the LOR counts may refer to counts of line of response in annihilation events at a time interval. The component-normalized counts may refer to LOR counts corrected by performing a component-based normalization. The LOR counts and component-normalized counts may be acquired in real time in a component-based normalization process.

In some embodiments, the component-normalized counts may be different from the LOR counts. In some embodiments, the LOR counts corrected by self-norm coefficient (i.e., self-normalized LOR counts) may be the same as the LOR counts. The difference between the LOR counts and the component-normalized counts may lead to different SUVs between the PET image corrected by a self-normalization and the PET image corrected by a component-based normalization.

In 904, a scale factor may be determined based on the LOR counts and the component-normalized counts at a time interval. The scale factor may be determined by, for example, the determination unit 520. The scale factor may be determined based on the LOR counts at the time interval and the component-normalized counts corresponding to LOR counts. In some embodiments, the scale factor may be a ratio between the LOR counts and the component-normalized counts. In some embodiments, the scale factor may be stored in a LUT. The LUT may provide a correspondence relationship between single count rates and scale factors.

It should be noted that the above description is provided for the purposes of illustration, not intended to limit the scope of the present disclosure. For persons having ordinary skills in the art, multiple variations and modifications may be reduced to practice in the light of the present disclosure. For example, the process 900 may further include acquiring LOR counts corresponding to a plurality of time intervals and component-normalized counts corresponding to the plurality of time intervals. A set of scale factors may be determined. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A method implemented on at least one computing device each of which has at least one processor and storage, the method comprising:
    acquiring first PET data at a time interval;
    acquiring a plurality of correction coefficients, wherein the plurality of correction coefficients include a normalization coefficient corresponding to the first PET data, and a scale factor determined based at least in part on the normalization coefficient;
    correcting the first PET data based on the plurality of correction coefficients; and
    reconstructing an image based on the corrected first PET data.

2. The method of claim 1, wherein the normalization coefficient is determined based on a component-based normalization correction method.

3. The method of claim 1, wherein acquiring the plurality of correction coefficients includes:
    acquiring a single count rate at the time interval; and
    acquiring the plurality of correction coefficients corresponding to the single count rate.

4. The method of claim 3, wherein acquiring the plurality of correction coefficients corresponding to the single count rate includes:
    determining a relationship between the single count rate and the plurality of correction coefficients; and
    determining the plurality of correction coefficients corresponding to the single count rate based on the relationship between the single count rate and the plurality of correction coefficients.

5. The method of claim 4, wherein determining the relationship between the single count rate and the plurality of correction coefficients includes:
    acquiring a first look up table, wherein the first look up table indicates a relationship between the single count rate and the normalization coefficient corresponding to the first PET data.

6. The method of claim 4, wherein determining the relationship between the single count rate and the plurality of correction coefficients includes:
    acquiring a second look up table, wherein the second look up table indicates a relationship between the single count rate and the scale factor.

7. The method of claim 6, wherein the second look up table is determined according to a scale factor determination method, the method includes:
    determining line of response counts based on the first PET data;
    determining normalized counts based on the line of response counts and the normalization coefficient; and
    determining the scale factor corresponding to the first PET data based on the line of response counts and the normalized counts.

8. The method of claim 6, wherein the second look up table is determined according to a scale factor determination method, the method includes:
acquiring second PET data at a plurality of time intervals;
acquiring a plurality of first normalization coefficients corresponding to the plurality of time intervals, respectively;
acquiring a plurality of second normalization coefficients corresponding to the plurality of time intervals, respectively;
reconstructing a first set of images based on the second PET data and the plurality of first normalization coefficients;
reconstructing a second set of images based on the second PET data and the plurality of second normalization coefficients;
determining a set of scale factors based on the first set of images and the second set of images; and
determining a scale factor corresponding to the first PET data based on the set of scale factors.

9. The method of claim 8, wherein the first normalization coefficients are determined based on a self-normalization correction method, and the second normalization coefficients are determined based on a component-based normalization correction method.

10. A system, comprising:
at least one non-transitory storage medium including a set of instructions; and
at least one processor configured to communicate with the at least one storage media, wherein when executing the set of instructions, the at least one processor is configured to cause the system to:
acquire PET data at a time interval;
acquire a plurality of correction coefficients, wherein the plurality of correction coefficients include a normalization coefficient corresponding to the PET data, and a scale factor determined based at least in part on the normalization coefficient;
correct the PET data based on the plurality of correction coefficients; and
reconstruct an image based on the corrected PET data.

11. The system of claim 10, wherein the normalization coefficient is determined based on a component-based normalization correction method.

12. The system of claim 10, wherein to acquire the plurality of correction coefficients, the at least one processor is configured to cause the system to:
acquire a single count rate at the time interval; and
acquire the plurality of correction coefficients corresponding to the single count rate.

13. The system of claim 12, wherein to acquire the plurality of correction coefficients corresponding to the single count rate, the at least one processor is configured to cause the system to:
determine a relationship between the single count rate and the plurality of correction coefficients; and
determine the plurality of correction coefficients corresponding to the single count rate based on the relationship between the single count rate and the plurality of correction coefficients.

14. The system of claim 13, wherein to determine the relationship between the single count rate and the plurality of correction coefficients, the at least one processor is configured to cause the system to:
acquire a first look up table, wherein the first look up table indicates a relationship between the single count rate and the normalization coefficient corresponding to the PET data.

15. The system of claim 13, wherein to determine the relationship between the single count rate and the plurality of correction coefficients, the at least one processor is configured to cause the system to:
acquire a second look up table, wherein the second look up table indicates a relationship between the single count rate and the scale factor.

16. The system of claim 15, wherein the second look up table is determined according to a scale factor determination method, the method includes:
determining line of response counts based on the first PET data;
determining normalized counts based on the line of response counts and the normalization coefficient; and
determining the scale factor corresponding to the first PET data based on the line of response counts and the normalized counts.

17. The system of claim 15, wherein the second look up table is determined according to a scale factor determination method, the method includes:
acquiring second PET data at a plurality of time intervals;
acquiring a plurality of first normalization coefficients corresponding to the plurality of time intervals, respectively;
acquiring a plurality of second normalization coefficients corresponding to the plurality of time intervals, respectively;
reconstructing a first set of images based on the second PET data and the plurality of first normalization coefficients;
reconstructing a second set of images based on the second PET data and the plurality of second normalization coefficients;
determining a set of scale factors based on the first set of images and the second set of images; and
determining a scale factor corresponding to the first PET data based on the set of scale factors.

18. The system of claim 17, wherein the first normalization coefficients are determined based on a self-normalization correction method, and the second normalization coefficients are determined based on a component-based normalization correction method.

19. A non-transitory computer readable medium storing instructions, the instructions, when executed by a computing device, causing the computing device to implement a method, comprising:
acquiring PET data at a time interval;
acquiring a plurality of correction coefficients, wherein the plurality of correction coefficients include a normalization coefficient corresponding to the PET data, and a scale factor determined based at least in part on the normalization coefficient;
correcting the PET data based on the plurality of correction coefficients; and
reconstructing an image based on the corrected PET data.

* * * * *